United States Patent
Yahata et al.

(10) Patent No.: US 8,865,073 B2
(45) Date of Patent: Oct. 21, 2014

(54) AIR PURIFIER AND TOTAL ORGANIC CARBON MEASURING DEVICE USING THE AIR PURIFIER

(75) Inventors: Masahito Yahata, Kyoto (JP); Takeshi Iharada, Kyoto (JP); Katsutoshi Fujii, Kyoto (JP)

(73) Assignee: Shimadzu Corporation, Kyoto (JP)

(*) Notice: Subject to any disclaimer, the term of this patent is extended or adjusted under 35 U.S.C. 154(b) by 0 days.

(21) Appl. No.: 13/523,434

(22) Filed: Jun. 14, 2012

(65) Prior Publication Data

US 2013/0336840 A1    Dec. 19, 2013

(51) Int. Cl.
| | |
|---|---|
| *G01N 15/06* | (2006.01) |
| *G01N 33/00* | (2006.01) |
| *G01N 33/48* | (2006.01) |
| *B01D 53/22* | (2006.01) |
| *B01D 59/12* | (2006.01) |

(52) U.S. Cl.
USPC .................................. 422/68.1; 96/8; 96/132

(58) Field of Classification Search
CPC combination set(s) only.
See application file for complete search history.

(56) References Cited

U.S. PATENT DOCUMENTS

| | | | | | |
|---|---|---|---|---|---|
| 4,559,066 | A | * | 12/1985 | Hunter et al. | 96/117.5 |
| 2008/0271606 | A1 | * | 11/2008 | Holmes et al. | 96/132 |

FOREIGN PATENT DOCUMENTS

| | | | | |
|---|---|---|---|---|
| GB | 2248409 | A | * | 4/1992 |
| GB | 2479257 | A | * | 10/2011 |
| JP | 11-156142 | A | | 6/1999 |
| JP | 2008-139229 | A | | 6/2008 |
| JP | 2008139229 | A | * | 6/2008 |

OTHER PUBLICATIONS

Japanese Office Action issued by the Japanese Patent Office in Japanese Patent Application No. 2010-092004 dated Jul. 16, 2013.

* cited by examiner

*Primary Examiner* — Jill Warden
*Assistant Examiner* — Julie Tavares
(74) *Attorney, Agent, or Firm* — Sughrue Mion, PLLC

(57) ABSTRACT

An air purifier includes a pump that supplies air to an air purifying unit, a filter arranged at an outlet of the air purifying unit, and pipes that connect these components. The air purifying unit includes an activated carbon tube constituted by a glass tube filled with granular activated carbon, and a soda lime tube constituted by a glass tube filled with granular soda lime. According to a preferred embodiment, three each of the activated carbon tubes and the soda lime tubes are provided, and the activated carbon tubes and the soda lime tubes are connected alternately in series by tubes so that one activated carbon tube is arranged at a most upstream part and one soda lime tube is arranged at a most downstream part.

4 Claims, 2 Drawing Sheets

AIR PURIFIER AND TOTAL ORGANIC CARBON MEASURING DEVICE USING THE AIR PURIFIER

TECHNICAL FIELD

The present invention relates to an air purifier for generating air from which carbon dioxide has been removed and, as one example of a use of the air purifier, a total organic carbon (TOC) measuring device that uses the air purifier. Air that has a low carbon dioxide content can be used, for example, for aeration treatment for removing inorganic carbon (IC) that is present in sample water collected in a TOC measuring device.

BACKGROUND ART

A TOC measuring device measures the amount of organic carbon of sample water by subjecting organic carbon contained in the sample water to oxidative decomposition to convert the organic carbon to carbon dioxide, and thereafter measuring the carbon dioxide concentration. Inorganic carbon is contained in sample water prior to subjecting the organic carbon to oxidative decomposition, and total carbon (TC) can be measured by converting the total carbon to carbon dioxide in that state and measuring the carbon dioxide concentration. TOC can also be determined as (TC−IC) by individually measuring TC and IC. On the other hand, when it is attempted to directly measure TOC, a measurement value of organic carbon in a case where IC has not been removed will be greater than the actual value. Therefore, a TOC measuring device is provided with an inorganic carbon removal unit to remove pre-existing inorganic carbon from sample water.

A common treatment that is performed in an inorganic carbon removal unit is an aeration treatment that supplies an aeration gas (sparge gas) to sample water (for example, see Patent Literature 1). To supply an aeration gas to this kind of inorganic carbon removal unit, conventionally, a high purity air cylinder in which the concentration of carbon dioxide and TOC is extremely low is connected to the device, or an air purifier is installed that purifies air by removing carbon dioxide and TOC from the air by combusting the air at a temperature between 700 and 900° C. to convert TOC in the air to carbon dioxide and passing the air through soda lime to cause the soda lime to absorb the carbon dioxide or the like.

CITATION LIST

Patent Literature

[Patent Literature 1] Japanese Patent Laid-Open No. 2008-139229

SUMMARY OF INVENTION

Problems to be Solved by the Invention

However, when a high purity air cylinder is connected to a TOC measuring device, a problem is that the cylinder must be replaced when the high purity air cylinder runs out of high purity air, and thus maintenance costs increase due to expenses that arise when replacing the cylinder. Further, in the case of an air purifier that passes air through soda lime after combusting the air, a problem is that a large installation area is required because a combustion furnace is needed to combust the air.

Thus, an object of the present invention is to provide an air purifier and a TOC measuring device that require a small installation area and for which maintenance costs are also reduced.

Means for Solving the Problems

An air purifier according to the present invention includes an air purifying unit in which a soda lime tube comprising a container that has an inlet port and an outlet port and that is filled with granular soda lime, and an activated carbon tube comprising a container that has an inlet port and an outlet port and that is filled with granular activated carbon are connected in series, and purifies air by passing the air through the soda lime tube and the activated carbon tube of the air purifying unit.

Activated carbon mainly adsorbs TOC and soda lime mainly adsorbs carbon dioxide, and therefore TOC and carbon dioxide can be efficiently removed from air by providing the activated carbon and soda lime in units of a fixed amount and alternately connecting the activated carbon and soda lime units.

In this connection, in comparison to soda lime, large amounts of carbon dioxide and TOC are originally adsorbed on activated carbon. If an activated carbon tube is arranged at a most downstream part of an air purifier, in some cases the carbon dioxide or TOC that had been originally adsorbed on the activated carbon emerges together with purified air. Therefore, it is preferable to connect a soda lime tube as the tube at the most downstream part of the air purifier. It is thereby possible to cause carbon dioxide that has emerged from an activated carbon tube to be adsorbed by soda lime.

When an air purifying unit is constructed by connecting one soda lime tube and one activated carbon tube in series, there are very rare cases in which carbon dioxide or TOC in air is not adsorbed by the air purifying unit and emerges from the air purifying unit, and if such air that contains carbon dioxide or TOC is supplied to a measuring device such as a TOC measuring device, an accurate measurement will not be possible. Consequently, it is preferable that the air purifying unit includes two or more soda lime tubes and activated carbon tubes, respectively, and that the soda lime tubes and activated carbon tubes are connected in an alternating manner. Thus, even if carbon dioxide or TOC exists that has not been adsorbed by a soda lime tube or an activated carbon tube on an upstream side, the carbon dioxide or TOC can be adsorbed by a soda lime tube or an activated carbon tube on a side that is further downstream. Furthermore, by alternately connecting soda lime tubes and activated carbon tubes, part of the activated carbon surface becomes alkaline, which provides an added capability to adsorb an acidic organic gas or carbon dioxide, and the alternate connection allows efficient removal of TOC and carbon dioxide.

A TOC measuring device according to the present invention includes: an inorganic carbon removal unit that removes inorganic carbon contained in sample water by performing aeration treatment by means of an aeration gas by aerating the sample water with the aeration gas; an oxidation reaction unit that converts organic carbon in the sample water that has passed through the inorganic carbon removal unit to carbon dioxide; and a carbon dioxide measuring unit that measures a carbon dioxide concentration in the sample water that has passed through the oxidation reaction unit; wherein an air purifier according to the present invention is connected to the inorganic carbon removal unit, and air that is purified by the air purifier is supplied to the sample water as the aeration gas.

Advantageous Effects of Invention

The air purifier according to the present invention includes an air purifying unit in which a soda lime tube constituted by a container that has an inlet port and an outlet port and that is filled with granular soda lime, and an activated carbon tube constituted by a container that has an inlet port and an outlet port and that is filled with granular activated carbon are connected in series, and since the air purifier does not require a high purity air cylinder or a combustion furnace, installation costs can be decreased and the installation area can be reduced in comparison to a conventional air purifier.

The TOC measuring device according to the present invention is a device in which an aeration gas is supplied to an inorganic carbon removal unit using the air purifier according to the present invention, and hence the TOC measuring device can be made in a smaller size and with lower maintenance costs compared to a conventional TOC measuring device.

MODE FOR CARRYING OUT THE INVENTION

Figure 1:
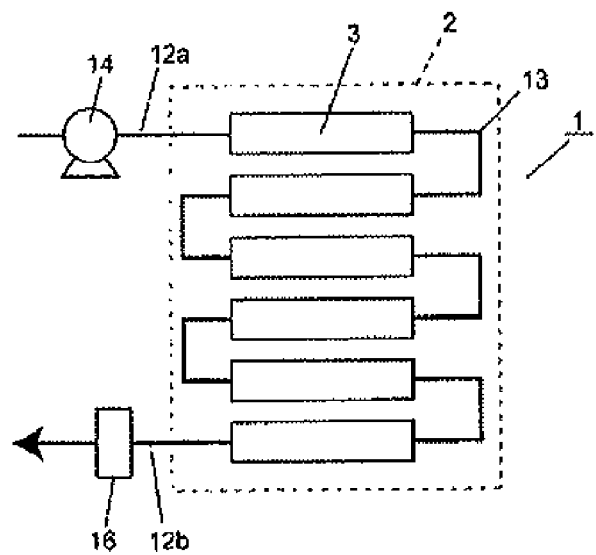
FIG. 1 is a flow diagram that schematically illustrates one embodiment of an air purifier.

One embodiment of the air purifier will now be described using FIG. 1 and FIG. 2.

An air purifier 1 includes a pump 14 that supplies air to an air purifying unit 2, a filter 16 that is arranged at an outlet of the air purifying unit 2, and pipes 12a and 12b that connect these components. In the air purifying unit 2, a plurality of carbon dioxide absorption tubes 3 are connected in series by tubes 13. The pump 14 is provided for the purpose of drawing in air and feeding the air to the air purifying unit 2, and the filter 16 is provided for the purpose of removing solid matter from air that has passed through the air purifying unit 2.

Figure 2:
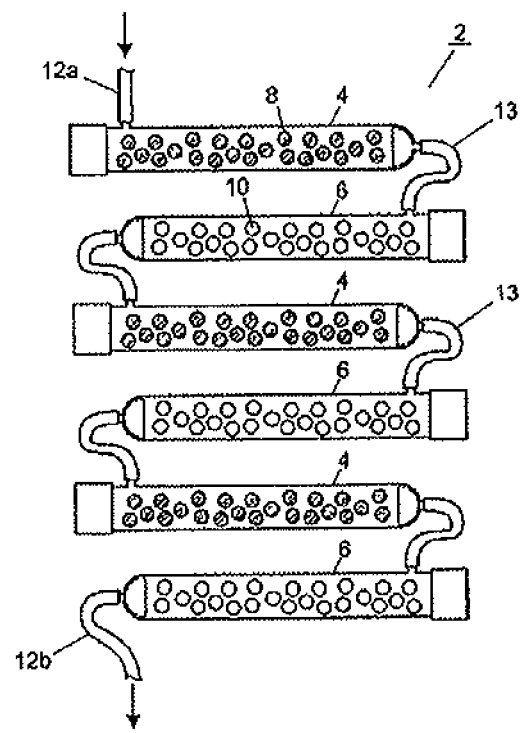
FIG. 2 is a plan view that illustrates an air purifying unit according to the same embodiment in detail.

As shown in FIG. 2, as the carbon dioxide absorption tubes 3, the air purifying unit 2 includes activated carbon tubes 4 that are each constituted by, for example, a glass tube with an inner diameter of 10 to 20 mm and a length of approximately 15 cm that is filled with 20 to 50 g of granular activated carbon 8 with a diameter of approximately 1 to 3 mm, and soda lime tubes 6 that are each constituted by, for example, a glass tube with an inner diameter of 10 to 20 mm and a length of approximately 15 cm that is filled with 20 to 50 g of granular soda lime 10 with a diameter of approximately 1 to 3 mm. In this connection, a container constituting each of the activated carbon tubes 4 and the soda lime tubes 6 that contain the activated carbon 8 or the soda lime 10 may also be composed of an inorganic material other than glass.

One end of the respective glass tubes constituting the activated carbon tubes 4 and the soda lime tubes 6 is sealed with a cap, and a protrusion-shaped opening is provided in a side wall in a vicinity thereof. A protrusion-shaped opening is also provided in the other end of the respective glass tubes. These protrusion-shaped openings are inserted into a hole of the relevant tube 13, and are connected to another activated carbon tube 4 or soda lime tube 6 through the tube 13. In each glass tube, an opening on an upstream side is an inlet port and an opening on a downstream side is an outlet port. The pipe 12a is inserted into the protrusion-shaped opening of the activated carbon tube 4 on the most upstream side, and the pipe 12a is connected to the pump 14. The pipe 12b is inserted into the protrusion-shaped opening of the soda lime tube 6 on the most downstream side, and the pipe 12b is connected to the filter 16. Three each of the activated carbon tubes 4 and the soda lime tubes 6 are provided, and these tubes are connected alternately in series by the tubes 13 so that one activated carbon tube 4 is arranged at a most upstream part and one soda lime tube 6 is arranged at a most downstream part.

In this connection, as the activated carbon 8 that is filled in the activated carbon tubes 4, it is preferable to, as much as possible, use activated carbon that has been previously baked for 2 to 3 hours at 500 to 600° C. under an inert gas atmosphere so as to reduce an adsorption amount of carbon dioxide or TOC thereof at a stage prior to filling the activated carbon into the activated carbon tubes 4. The soda lime 10 that is filled in the soda lime tubes 6 is preferably soda lime with a moisture content of approximately 2 to 10%, and it is preferable to use soda lime that has been wrapped in an inorganic material such as an aluminum pouch so that the soda lime is not allowed to come in contact with air and adsorb carbon dioxide before the soda lime is filled in the soda lime tubes 6.

In the air purifier 1, the activated carbon tubes 4 mainly act to adsorb organic gases contained in air, and the soda lime tubes 6 mainly act to adsorb carbon dioxide.

In this connection, although according to this embodiment three activated carbon tubes 4 and three soda lime tubes 6 are provided and connected in an alternating manner, the number of the activated carbon tubes 4 and the soda lime tubes 6 may be one, two, or four or more. Further, the activated carbon tubes 4 and the soda lime tubes 6 need not necessarily be connected in an alternating manner. For example, the carbon dioxide absorption tubes 3 may be connected in the order of activated carbon tube 4—activated carbon tube 4—soda lime tube 6—soda lime tube 6, or in the order of soda lime tube 6—activated carbon tube 4—activated carbon tube 4—soda lime tube 6. Note that the carbon dioxide absorption tube 3 at the most downstream position is preferably the soda lime tube 6. This is because, since an initial carbon dioxide adsorption amount of activated carbon is greater than that of soda lime, the carbon dioxide of the activated carbon is prevented from emerging from the air purifier 1 together with purified air.

The air purifier 1 causes air that is supplied by the pump 14 to pass in turn through the activated carbon tubes 4 and the soda lime tubes 6 of the air purifying unit 2 to thereby remove carbon dioxide and TOC contained in the air by adsorbing the carbon dioxide and TOC on the activated carbon 8 and the soda lime 10, and thus the air purifier 1 can purify the air to obtain air that has a low content of carbon dioxide and TOC. The air purifier 1 constituted in this manner by only a plurality of the activated carbon tubes 4 and the soda lime tubes 6, the pump 14, and the filter 16 is smaller and less expensive than an air purifier that adopts a method in which air is combusted in a combustion furnace and thereafter carbon dioxide is absorbed by soda lime, and can be integrated into a device such as a TOC measuring device without increasing the size of the device.

Figure 3:
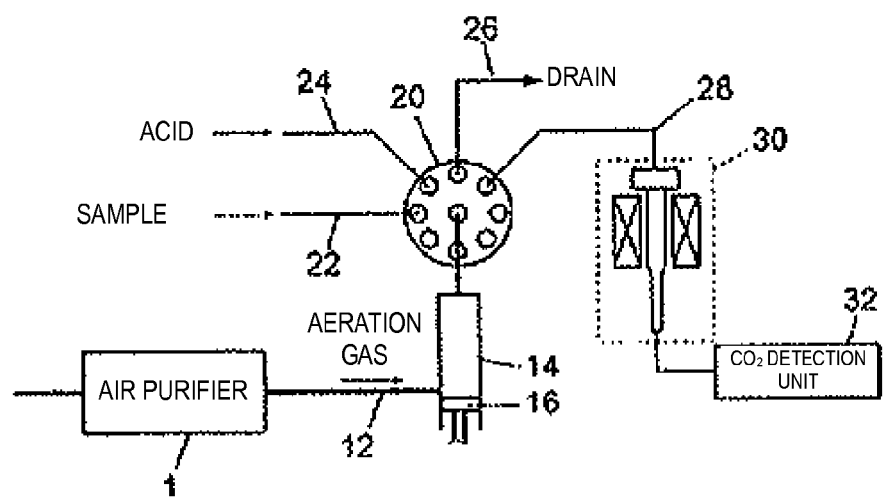
FIG. 3 is a flow diagram that schematically illustrates one embodiment of a TOC measuring device.

An example of a TOC measuring device that uses the above-described air purifier 1 will now be described using FIG. 3.

A switching valve 20 for switching channels includes a common port that is provided in the center thereof and a plurality of ports that are selectively connected to the common port. A syringe 14 is connected to the common port of the switching valve 20, and a sample channel 22, an acid supply channel 24, a drain channel 26, and a measurement channel 28 that links to an oxidation reaction unit 30 are connected to ports that are selectively connected to the common port, respectively. The oxidation reaction unit 30 is connected to a $CO_2$ detection unit 32. A suction/discharge opening of the syringe 14 faces upwards, and a plunger 16 is arranged so as to slide in the vertical direction in the syringe 14. The air purifier 1 is connected through a pipe 12 to a lower part of an inner space of the syringe 14, and a configuration is adopted so that air from the air purifier 1 is supplied into the syringe 14 when the plunger 16 is below a connection position of the pipe.

According to this TOC measuring device, first the switching valve 20 is switched so as to connect the syringe 14 and the sample channel 22, and in a state in which the plunger 16 is below the connection position of the pipe 12, the plunger 16 is driven to a suction side to suck a sample into the syringe 14. Next, the switching valve 20 is switched so as to connect the syringe 14 and the acid supply channel 24, and the plunger 16 is driven further to the suction side to add acid to the sample in the syringe 14.

Subsequently, the switching valve 20 is switched so as to connect the syringe 14 and the drain channel 26, and aeration gas is supplied from the air purifier 1 into the syringe 14 to subject the sample in the syringe 14 to an aeration treatment. As a result of this aeration treatment, inorganic carbon contained in the sample is discharged to outside through the drain channel 26. After the aeration treatment ends, the plunger 16 is driven to a discharge side so as to discharge a gaseous phase that is at an upper part inside the syringe 14 from the drain channel 26, and thereafter the switching valve 20 is switched so as to connect the syringe 14 and the measurement channel 28, and the plunger 16 is then driven further to the discharge side to inject the sample into the oxidation reaction unit 30.

The sample that has passed through the oxidation reaction unit 30 is introduced into the $CO_2$ detection unit 32. Total organic carbon contained in the sample that is injected into the oxidation reaction unit 30 is converted to carbon dioxide, and the concentration of carbon dioxide into which the total organic carbon has been converted is detected by the $CO_2$ detection unit 32. Total organic carbon concentrations of the sample and detection values for carbon dioxide concentration that are detected by the $CO_2$ detection unit 32 are previously associated with each other by means of a calibration curve, and thus the total organic carbon concentration can be measured by detecting the carbon dioxide concentration of the sample.

Table 1 shows results of TOC measurements performed over one month (31 days) using the TOC measuring device of the above-described embodiment (described as <Embodiment> in Table 1) and a TOC measuring device that used a high purity air cylinder instead of the air purifier 1 of the above-described embodiment (described as <Comparison Example> in Table 1) in a case where pure water was used as a sample and the temperatures (described as "Purification column temperature" in Table 1) of the air purifier 1 and the high purity air cylinder were 7° C., 25° C., and 40° C. The measurement conditions were an aeration gas supply flow rate of 100 ml/min, an aeration time of 90 seconds per single measurement, and a sample amount of 2000 μL.

TABLE 1

| Purification column temperature | <Embodiment> Measurement value (ppb) | <Comparison Example> Measurement value (ppb) | Measurement value difference (ppb) |
|---|---|---|---|
| 7° C. | 1.58 | 1.57 | 0.01 |
| 25° C. | 2.62 | 1.86 | 0.76 |
| 40° C. | 1.41 | 1.11 | 0.30 |

As shown in Table 1, when the purification column temperature was 7° C., 25° C., and 40° C., a difference between a measurement value of the Embodiment and a measurement value of the Comparison Example was not greater than 1 ppb in each case. It is considered that an allowable error of a measurement value in a TOC measuring device is 1 ppb or less when measuring pure water, and the above-described results satisfy this condition for each purification column temperature. It could thus be confirmed that the air purifier 1 of the above embodiment has performance that can withstand use for one month in a TOC measuring device.

REFERENCE SIGNS LIST

1 Air purifier
2 Air purifying unit
3 Carbon dioxide absorption tube
4 Activated carbon tube
6 Soda lime tube
8 Activated carbon
10 Soda lime
12 Pipe
13 Tube
14 Syringe
16 Plunger
20 Switching valve
22 Sample channel
24 Acid supply channel
26 Drain channel
28 Measurement channel
30 Oxidation reaction unit
32 $CO_2$ detection unit

What is claimed is:

1. An air purifier comprising:
an air purifying unit with at least one soda lime tube comprising a container that has an inlet port and an outlet port and that is filled with contents consisting essentially of granular soda lime, and at least one activated carbon tube comprising a container that has an inlet port and an outlet port and that is filled with contents consisting essentially of granular activated carbon;
wherein the at least one soda lime tube and the at least one activated carbon tube are connected in series with a connecting tube;
wherein the air purifier purifies air by passing the air through the soda lime tube and the activated carbon tube of the air purifying unit,
wherein the air purifying unit comprises two or more of the soda lime tubes and the activated carbon tubes, respectively, and the soda lime tubes and the activated carbon tubes are connected in an alternating manner.

2. The air purifier according to claim 1, wherein a tube connected at a most downstream part of the air purifying unit is one of the soda lime tubes.

3. The air purifier according to claim 1, wherein the at least one soda lime tube has a length of an airflow path from the inlet port to the outlet port that is longer than a width of the at least one soda lime tube in a direction substantially perpendicular to an axis of the at least one soda lime tube, and the at least one activated carbon tube has a length of an airflow path from the inlet port to the outlet port that is longer than a width of the at least one activated carbon tube in a direction substantially perpendicular to an axis of the at least one activated carbon tube.

4. A total organic carbon measuring device comprising: an inorganic carbon removal unit that removes inorganic carbon contained in sample water by performing aeration treatment to the sample water with the aeration gas; an oxidation reaction unit that converts organic carbon in the sample water that has passed through the inorganic carbon removal unit to carbon dioxide; and a carbon dioxide measuring unit that measures a carbon dioxide concentration in the sample water that has passed through the oxidation reaction unit;

wherein an air purifier according to claim 1 is connected to the inorganic carbon removal unit, and air that is purified by the air purifier is supplied to the sample water as the aeration gas.

* * * * *